United States Patent [19]

Spear et al.

[11] Patent Number: 5,801,819
[45] Date of Patent: Sep. 1, 1998

[54] DISTINGUISHING NATURAL FROM SYNTHETIC DIAMOND

[75] Inventors: Paul Martyn Spear, Maidenhead; Christopher Welbourn, Waltham St Lawrence, both of United Kingdom

[73] Assignee: Gersan Establishment, Liechtenstein

[21] Appl. No.: 793,727

[22] PCT Filed: Aug. 18, 1995

[86] PCT No.: PCT/GB95/01968

§ 371 Date: May 5, 1997

§ 102(e) Date: May 5, 1997

[87] PCT Pub. No.: WO96/07894

PCT Pub. Date: Mar. 14, 1996

[30] Foreign Application Priority Data

Sep. 19, 1994 [GB] United Kingdom ............ 9417665

[51] Int. Cl.$^6$ ................................ G01N 21/87
[52] U.S. Cl. ............ 356/30; 250/461.1; 250/372; 209/578
[58] Field of Search ............ 356/30; 250/461.1, 250/458.1, 459.1, 461.2, 372; 209/577, 579, 589, 578

[56] References Cited

U.S. PATENT DOCUMENTS

| | | | |
|---|---|---|---|
| 4,019,060 | 4/1977 | Woodman | 250/461 |
| 4,034,066 | 7/1977 | Strong et al. | 423/446 |
| 4,073,380 | 2/1978 | Strong et al. | 206/219 |
| 4,200,801 | 4/1980 | Schuresko | 250/458 |
| 4,394,580 | 7/1983 | Gielisse | 250/461.1 |
| 4,653,081 | 3/1987 | Sipila et al. | 378/45 |
| 5,118,181 | 6/1992 | Yifrach et al. | 356/30 |
| 5,146,288 | 9/1992 | Russell | 356/30 |
| 5,206,699 | 4/1993 | Stewart et al. | 356/30 |

FOREIGN PATENT DOCUMENTS

| | | | |
|---|---|---|---|
| 0 056 426 | 7/1982 | European Pat. Off. | |
| 0 064 842 | 11/1982 | European Pat. Off. | |
| 0 071 462 | 2/1983 | European Pat. Off. | |
| 0 425 426 A3 | 5/1991 | European Pat. Off. | |
| 1384813 | 2/1975 | United Kingdom | 356/30 |
| 1 561 054 | 2/1980 | United Kingdom | |
| 2 089 029 | 6/1982 | United Kingdom | |
| 2 121 535 | 6/1982 | United Kingdom | |
| 2 215 041 | 9/1989 | United Kingdom | |
| 2 219 079 | 11/1989 | United Kingdom | |
| 2 267 147 | 11/1993 | United Kingdom | |
| WO 83/00389 | 2/1983 | WIPO | |
| WO 88/01378 | 2/1988 | WIPO | |
| WO 88/05534 | 7/1988 | WIPO | |
| WO 91/16617 | 10/1991 | WIPO | |
| WO 93/23742 | 11/1993 | WIPO | |
| WO 94/20837 | 9/1994 | WIPO | |

OTHER PUBLICATIONS

"Antwerp Facets", Oct. 1993, p. 25.
"Antwerp Gems", 1993, vol. 4, No. 2, pp. 31–33.
"Diamonds", a book by Eric Bruton, p. 409.
Woods and Lang Paper, Journal of Crystal Growth 28 (1975), pp. 215–226.
Walsh et al. Paper, Journal of Lujinescence 4 (1971), pp. 369–392.

(List continued on next page.)

Primary Examiner—Hoa Q. Pham
Attorney, Agent, or Firm—Cesari and McKenna, LLP

[57] ABSTRACT

In order to provide a simple, safe and compact apparatus for distinguishing natural, colorless, or near-colorless diamond from synthetic diamond, the apparatus is equipped with a chamber in which a flash lamp irradiates a stationary diamond with irradiation which has a substantial component of ultra-violet light below 250 nm or 255 nm. The intensity of phosphorescence emitted by the diamond after irradiation by the lamp is measured by a photomultiplier tube which sends a signal to a microprocessor. There is a visual display of the elapsed time for the phosphorescence intensity to decrease to a threshold value. The diamond is classified as probably natural if it has no phosphorescence or a short phosphorescence time.

19 Claims, 2 Drawing Sheets

OTHER PUBLICATIONS

Shigley et al. Paper, Gems & Gemology, vol. 23, 1987, pp. 187–206.

Rooney et al. Paper, Gems & Gemology, Spring 1993, pp. 38–45.

Ponahlo Paper, Journal of Gemology 1992 23, 1 pp. 3–17.

Burns et al. Paper –Growth Sector Dependence on Optical Features in Large Synthetic Diamonds –Journal of Crystal Growth 104 (1990), pp. 257–279.

Anderson & Jobbins Book –Gem Testing, 10th Edition, Butterworth, pp. 124, 202–205.

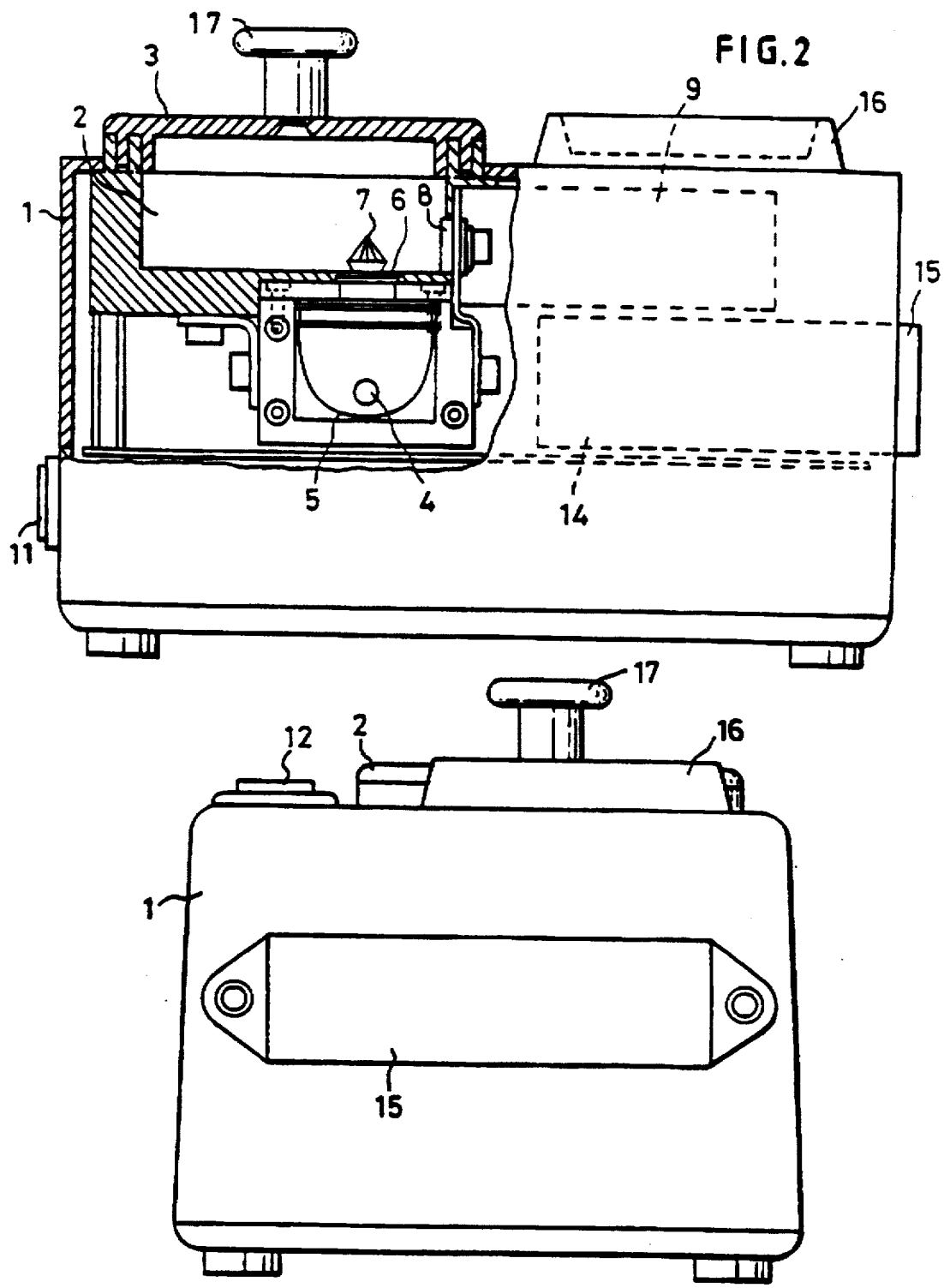

DISTINGUISHING NATURAL FROM SYNTHETIC DIAMOND

BACKGROUND OF THE INVENTION

The present invention relates to distinguishing natural colourless and near-colourless diamond from synthetic colourless or near-colourless diamond. By colourless or near-colourless is meant diamonds which are colour graded from D up to N (inclusive). It is desirable to provide apparatus which is small, compact, safe, and simple to operate.

EP 0 425 426A discloses apparatus for fingerprinting gemstones, particularly diamonds, thereby enabling a specific diamond to be distinguished from other diamonds. The gemstone is excited by light irradiation, which can be ultraviolet light, and the spectrum of the emitted luminescence is detected by measuring the luminescence radiation at a plurality of preselected wavelengths. There is no suggestion of distinguishing natural diamond from synthetic diamond.

EP 0 071 462A describes distinguishing natural from synthetic gemstones, but there is no indication that diamonds are included. The sample gemstone is illuminated with very broad spectrum irradiation, and the total emitted radiation, including internal reflection and fluorescence, is analysed. In the specific example, the lamp used is an ultraviolet lamp with a principal peak at 255 nm, and in general it is indicated that electrons and ultraviolet irradiation can be used, amongst other irradiations.

THE INVENTION

The present invention provides apparatus for and a method of distinguishing natural diamond from synthetic diamond. Preferred and/or optional features of the invention are set forth.

The apparatus of the invention can be provided in a compact and easily portable form suitable for use in jeweller's retail premises, and can be simple and safe in use. Synthetic colourless or near-colourless diamonds can be identified with a high degree of confidence. The invention can also be used to classify as "probably synthetic" a colourless or near-colourless natural diamond that has a surface deposition of low-nitrogen synthetic (CVD) diamond that phosphoresces. Although the invention may not produce a certain classification, the classification which is achievable can confer significant economic benefit. The invention can be used in conjunction with any other method for distinguishing natural diamond from synthetic diamond, to provide a further check. The apparatus can provide a cheap, safe, objective and reproductive means of measuring the decay time of phosphorescence from a diamond.

For the purposes of the present application, phosphorescence denotes any process whereby radiation is emitted by a diamond after the diamond has ceased to be irradiated with ultraviolet light.

The phosphorescence period for diamond may be relatively short, for example milliseconds, or quite long, for example a number of seconds or even minutes. The invention is based upon the observation that there is a strong correlation between synthetic diamonds being colourless or near-colourless and having long phosphorescence decay times. A colourless or near-colourless diamond may be classified as "probably natural" if it has not phosphorescence (the majority of colourless or near-colourless natural diamonds exhibit no phosphorescence) or a short phosphorescence decay time; for example, the phosphorescence time of a natural colourless or near-colourless diamond may be a number of milliseconds or hundredths of a second or less. However, some rare colourless or near colourless natural diamonds of type IIa have phosphorescent times exceeding 1 second. The measured phosphorescence of colourless or near colourless synthetic diamonds consists of a short component (fast decay) and a long component (slow) decay). The fast decay component is typically less than about 1 s. The slow decay component is greater that 1 s and typically remains measurable for 20 s or more and in some cases up to several minutes. The slow decay component gives more useful results. A colourless or near-colourless diamond may be classified as "probably synthetic" and referred for further testing if it has a long phosphorescence time, for example a phosphorescence time of the order of tenths of a second, seconds, tens of seconds, or longer. A three category sort can be performed, namely "probably natural", "further examination" and "probably synthetic", those in the "further examination" category having decay times between the short and long decay times, or there can be a two category sort with no interval between the short and long decay times.

When observing the phosphorescence decay to a predetermined, fixed threshold, a short phosphorescence time can be defined as less than about 0.1 s or about 0.05 s and a long phosphorescence time can be defined as greater than about 0.1 s or about 0.2 s. The phosphorescence decay can be observed to a threshold which is a specific percentage of the initial or peak phosphorescence; if the percentage is high, say 90%, the long phosphorescence times can be defined as being somewhat shorter, say greater than about 0.05 s (or about 0.1 s, as above).

As visible and near infrared light does not induce phosphorescence in colourless or near-colourless diamonds, unfiltered light can be used, i.e. containing all the available UV light. However, there must be a substantial component, preferably at least about 5% of the total intensity reaching the demand, of UV below about 250 nm or below about 225 nm. There is a cut off of about 190 nm, due to absorption by air and by ultraviolet optics normally used. Phosphorescence in low-nitrogen synthetic diamonds is most efficiently excited if the irradiating radiation is ultraviolet rich with wavelengths below about 250 nm and preferably below about 225 nm—the peak phosphorescence intensity decreases rapidly above about 250 nm excitation. This is seen as an advantage as some of the rare natural diamonds that are known to phosphoresce do so more efficiently following excitation by wavelengths longer than 225 or 250 nm. In one mode of operation, wavelengths above say 250 nm are excluded from the irradiation and a number of natural diamonds known to phosphoresce following excitation with wavelengths only above 250 nm would be correctly classified as "probably natural".

The phosphorescence intensity will also depend upon the intensity of the irradiating radiation. In order to ensure uniform results, substantially the same irradiating radiation should be used for all diamonds.

Rapid cut-off of the irradiation is important. A shutter could be used with a continuous source but it is more convenient to use a flash lamp such as a xenon lamp.

The phosphorescence can be sensed using any suitable measuring device. The phosphorescence intensity may be sensed continuously or at a number of intervals. The phosphorescence may be simply observed by noting the phosphorescence time, ie the time required for the phosphorescence intensity to drop below a threshold. The threshold may be fixed at a present level e.g. on a display, if the phosphorescence intensity is measured. Alternatively, the threshold could be variable, for example a phosphorescence intensity equal to 90%, 50%, 20% or 10% of the initial peak phosphorescence intensity or of the phosphorescence intensity measured a specific time, say 0.2 s or 0.3 s, after the cessation of irradiation. If the observation technique is based upon the time for the signal to drop by a given factor, the size of the diamond is not important. However, in general, a size reference signal may be provided by the apparatus, e.g., by always adjusting the peak signal to the same value.

The apparatus of the invention can give a signal which allows the observer to study the variation with time of phosphorescence emitted by a diamond. This allows the operator to classify the diamond as set out above. A readout having a display which varies with the phosphorescence intensity may be provided. The display may be in arbitrary units. Alternatively, the apparatus may comprise means for analysing the variation with time of the phosphorescence intensity signal and for outputting a signal indicating that the diamond is probably natural or probably synthetic.

In a general sense, the diamond is located in that it is in a defined position when irradiated; preferably it will be stationary, but it need not be fixed in position and can merely be placed on a suitable substrate.

PREFERRED EMBODIMENT

The invention will be further described, by way of example only, with reference to the accompanying drawings, in which:

FIG. 2 is an elevation of the instrument, partly in section along the line II—II in FIG. 1; and FIG. 3 is a side view of the instrument.

Figure 1:
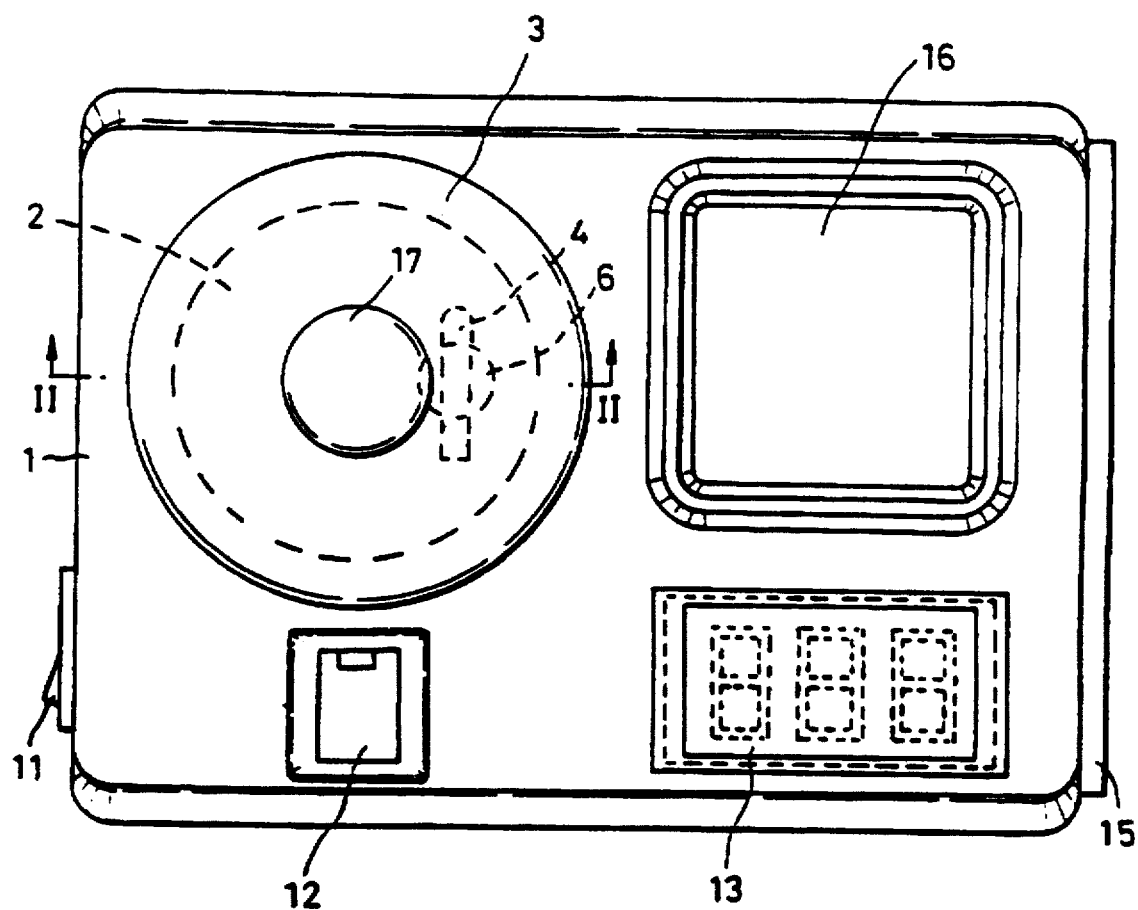
FIG. 1 is a plan view of an instrument in accordance with the invention.

The instrument has a casing 1 in which is mounted a chamber 2 having a light-tight, removeable lid 3. Below the chamber 2, there is means for irradiating in the form of a flash lamp 4. The preferred flash lamp 4 is a xenon lamp, for instance a 10 watt Heinmann DGS0610 lamp having a Heinmann UV glass envelope, supplied by Electrovalue Limited. Such a lamp 4 emits visible light and ultraviolet down to 215 nm, being rich in ultraviolet; about 8% of the total intensity (measured between 200 and 750 nm) is between 200 and 250 nm. An alternative, more expensive lamp 4 has a Heinmann quartz glass envelope, which emits light down to 160 nm; about 23% of the total intensity is between 190 and 250 nm.

The preferred operation provides a pulse of approximately 10 μs duration and approximately 0.1 J energy. The lamp 4 is powered by a high voltage inverter, discharge capacitor and trigger transformer (not shown) in the casing 1. The flash lamp 4 irradiates with high intensity radiation containing sufficient ultraviolet radiation to excite phosphorescence, the flash length approximately to the pulse length.

The flash lamp 4 has a reflector 5 and is positioned below a circular quartz glass window 6. If little visible light should be present in the irradiation, a single transmission filter (not shown) can be placed below the window 6, allowing through ultraviolet light substantially between 190 and 250 nm. A diamond sample 7 is placed on the window 6; the sample 7 need only be located to this extent, ie it need not be held in position, though it is advisable to ensure that all of the sample 7 is in direct view of the lamp 4. The chamber 2 has a further quartz glass window 8 permitting radiation from the diamond 7 to be sensed without filtering by a photomultiplier tube (PMT) in a photomultiplier module 9. The preferred photomultiplier module 9 is a Hamamatsu HL 120 PMT module, containing a PMT and a programmable high voltage power supply, supplied by Hamamatsu Photonics UK Ltd. The flash lamp 4 and the PMT are controlled by a microprocessor. The microprocessor could be included in the instrument but the instrument is preferably linked to a personal computer (PC) which provides the microprocessor function.

The drawings indicate an on-off switch 11, a start switch 12, a display 13, a battery compartment 14 with cover 15, and a tray 16 for holding stones. The lid 3 is shown with a handle 17 for manipulating the lid. An interlock (not shown) is provided to prevent operation of the flash lamp 4 when the lid 3 is open.

The PMT produces a signal which varies in time and which depends upon the intensity of radiation emitted by the sample 7. This signal is input to the microprocessor which in turn provides a signal to the display 13.

The procedure for using the instrument is as follows:

The sample 7 is placed on the window 6 and the chamber 2 is then sealed with the lid 3 so that no light enters the chamber 2.

The high voltage inverter charges the discharge capacitor to a fixed voltage. The lamp 4 is triggered using the trigger transformer. The PMT supplies a signal to the microprocessor representative of the luminous flux intensity in the chamber 2 at any given time. If the sample 7 phosphoresces after the illumination has ceased, the microprocessor provides a phosphorescence reading displayed upon the display 13 in arbitrary units. The observer can observe the variation with time of the phosphorescence intensity produced by the sample 7, as displayed by the display 13. For example, the observer may observe the time taken for the signal to drop to a given threshold, for example 0 on the display 13, or the time taken for the signal on the display 13 to reduce by a given factor, for example by 90%. The operator may classify the diamond on the basis of the signal shown by the display 13. If the display 13 shows a long phosphorescence time, the diamond is classified as "probably synthetic". If the phosphorescence time is short, the diamond is classified as "probably natural".

The microprocessor can automatically gives a read-out on the display 13 to indicate whether the sample 7 is natural or synthetic or to be subject to further testing and sorting. However, in the embodiment shown, the read-out of the display 1 gives the elapsed time since the termination of the flash and stops when a certain threshold is reached.

In one arrangement, the sample 7 is classified as:

natural diamond if no phosphorescence above a predetermined low threshold is detected after 1 s;

for further examination if phosphorescence above the threshold is detected between 1 s and 2 s;

synthetic if phosphorescence above the threshold is detected after 2 s.

The threshold can either be a fixed threshold, eg. 0.6 volts (assuming a peak of about 6 volts) representing certain luminous flux intensity in the chamber 2, or can be 10% of the peak phosphorescence emitted by the sample 7, as detected by the PMT. In this embodiment, to set the 6 volts for any one specimen 7, the peak intensity is measured a number of times, after corresponding flashes of the lamp 4, and the microprocessor adjusts the gain of the PMT until the peak is close to 6 volts. The sample 7 can then be tested. The peak phosphorescence was the luminous flux intensity say 0.2 s after the lamp flash, the 0.2 s delay being here due to the response of the photomultiplier module 9.

The microprocessor 10, pulse generator and display 13 may comprise digital or analogue electronics. The display 13 may comprise a 7-segment digital display as shown or any other representation of the phosphorescence intensity, for example a line whose length is proportional to the phosphorescence intensity.

In plan view, the instrument shown can have a size of about 100 mm×140 mm, and can thus be easily portable.

The present invention has been described above purely by way of example, and modifications can be made within the invention.

We claim:

1. Apparatus for distinguishing natural colourless or near-colourless diamond from synthetic colourless or near-colourless diamond, comprising:
   means for locating a diamond;
   means for irradiating the diamond with light which has a substantial component of its intensity in the form of ultraviolet light of a wavelength below about 250 nm;
   means responsive to the intensity of phosphorescence radiation emitted by the diamond, for producing a signal which varies with time and depends upon the intensity of phosphorescence radiation emitted by the diamond; and
   processing means responsive to said signal, for giving an indication dependent upon the relationship of the intensity of phosphorescence radiation and the time elapsed since the cessation of irradiation, thereby enabling the diamond to be classified.

2. The apparatus of claim 1, wherein the processing means comprises means for producing a visual indication representative of said signal.

3. The apparatus of claim 1 or 2 wherein there is no substantial component in the irradiation irradiating a diamond having a wavelength above about 250 nm.

4. The apparatus of claim 1, wherein the processor indicates the intensity of phosphorescence radiation after a predetermined time elapsed since the cessation of irradiation.

5. The apparatus of claim 1, wherein the processor indicates the time between the cessation of irradiation and the intensity of phosphorescence radiation dropping to a threshold value.

6. The apparatus of claim 5, wherein the threshold value is a predetermined proportion of the peak value or the intensity of phosphorescence radiation.

7. The apparatus of claim 1, wherein the light irradiating the diamond has a substantial component of its intensity in the form of ultraviolet light of a wavelength below about 225 nm.

8. The apparatus of claim 1, wherein the processor provides a size reference signal, to thereby compensate for the size of the diamond.

9. The apparatus of claim 1 or 2, wherein the diamond locating means provides for the diamond to be stationary when irradiated.

10. A method of distinguishing natural colorless or near-colorless diamond from synthetic colorless or near-colorless diamond, comprising
    the steps of using an apparatus in which a diamond is located,
    irradiating the diamond with light which has a substantial component of its intensity in the form of ultraviolet light of a wavelength below about 250 nm,
    detecting the intensity of phosphorescence radiation emitted by the diamond to produce a signal which varies with time and depends upon the intensity of phosphorescence radiation emitted by the diamond, and
    processing said signal to give an indication from which the diamond is classsified as probably natural if the diamond shows no phosphorescence or a short phosphorescence time.

11. Apparatus for distinguishing natural colorless or near-colorless diamond from synthetic colorless or near-colorless diamond comprising
    a support for locating a diamond;
    a light source for irradiating the diamond with light which has a substantial component of its intensity in the form of ultraviolet light of wavelength below about 250 nm;
    a sensor responsive to the intensity of phosphorescence radiation emitted by the diamond, for producing a signal which varies with time and depends upon the intensity of phosphorescence radiation emitted by the diamond, and
    a processor responsive to said signal, for giving an indication dependent upon the relationship of the intensity of phosphorescence radiation and the time elapsed since the cessation of irradiation, thereby enabling the diamond to be classified.

12. The apparatus of claim 11, wherein there is no substantial component in the irradiation irradiating the diamond having a wavelength above about 250 nm.

13. The apparatus of claim 11, wherein the irradiation irradiating the diamond has a substantial component of its intensity in the form of ultraviolet light of a wavelength below about 225 nm.

14. A method of distinguishing natural colorless or near-colorless diamond from synthetic colorless or near-colorless diamond, comprising:
    irradiating a diamond with light which has a substantial component of its intensity in the form of ultraviolet light of a wavelength of below about 250 nm;
    sensing the intensity of phosphorescence radiation emitted by the diamond and thereby producing a signal which varies with time and depends upon the intensity of phosphorescence radiation omitted by the diamond; and
    processing said signal to give an indication and using said indication to classify the diamond as probably natural if the diamond shows no phosphorescence or a short phosphorescence time.

15. The method of claim 14, comprising indicating the time between the cessation of radiation and the intensity of phosphorescence radiation dropping to a threshold value.

16. The method of claim 15, wherein the threshold value is a predetermined proportion of peak value of the intensity of phosphorescence radiation.

17. The method of claim 14, wherein there is no subatantial component in the irradiation irradiating the diamond having a wavelength above about 250 nm.

18. The method of claim 14, wherein the diamond is irradiated with light which has a substantial component of its intensity in the form of ultraviolet light of a wavelength below about 225 nm.

19. The method of claim 14, and comprising providing a size reference signal, thereby compensating for the size of the diamond.

* * * * *

UNITED STATES PATENT AND TRADEMARK OFFICE
CERTIFICATE OF CORRECTION

PATENT NO.   : 5,801,819
DATED        : September 1, 1998
INVENTOR(S)  : Spear, et al.

It is certified that error appears in the above-identified patent and that said Letters Patent is hereby corrected as shown below:

Column 5, line 36, delete "or 2".

Column 5, line 57, delete "or 2".

Column 6, line 11, after "comprising" insert --:--.

Column 6, line 21, change "," to --;--.

Signed and Sealed this

Sixth Day of July, 1999

*Attest:*

Q. TODD DICKINSON

*Attesting Officer*      Acting Commissioner of Patents and Trademarks